US010080824B2

(12) United States Patent
Dillon

(10) Patent No.: US 10,080,824 B2
(45) Date of Patent: Sep. 25, 2018

(54) ELONGATE TUBULAR MEMBER HAVING A CROSSOVER PORT

(71) Applicant: Cook Medical Technologies LLC, Bloomington, IN (US)

(72) Inventor: Travis E. Dillon, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 237 days.

(21) Appl. No.: 14/800,258

(22) Filed: Jul. 15, 2015

(65) Prior Publication Data

US 2016/0030707 A1 Feb. 4, 2016

Related U.S. Application Data

(60) Provisional application No. 62/031,455, filed on Jul. 31, 2014.

(51) Int. Cl.
| | | |
|---|---|---|
| *A61B 1/012* | (2006.01) | |
| *A61M 1/00* | (2006.01) | |
| *A61B 1/00* | (2006.01) | |
| *A61B 1/015* | (2006.01) | |

(Continued)

(52) U.S. Cl.
CPC ......... *A61M 1/008* (2013.01); *A61B 1/00119* (2013.01); *A61B 1/012* (2013.01); *A61B 1/015* (2013.01); *A61M 1/0058* (2013.01); *A61B 1/12* (2013.01); *A61M 3/0279* (2013.01)

(58) Field of Classification Search
CPC .............. A61B 1/0008; A61B 1/00091; A61B 1/00094; A61B 1/00135; A61B 1/00142; A61B 1/015; A61B 1/018; A61B 1/12; A61B 1/126; A61B 1/127; A61B 1/128; (Continued)

(56) References Cited

U.S. PATENT DOCUMENTS

| | | |
|---|---|---|
| 2,286,462 A | 5/1940 | Chaffin |
| 5,782,896 A | 7/1998 | Chen et al. |

(Continued)

FOREIGN PATENT DOCUMENTS

CN 202 843 567 U 4/2013

OTHER PUBLICATIONS

Search Report and Written Opinion for corresponding application No. PCT/US2015/040716 dated Oct. 8, 2015.

*Primary Examiner* — John P Leubecker
*Assistant Examiner* — Pamela F Wu
(74) *Attorney, Agent, or Firm* — Brinks Gilson & Lione

(57) ABSTRACT

A system may include an elongate tubular member having a first lumen, a second lumen, and a crossover port extending in between the first and second lumens such that the two lumens are in fluid communication with each other via the crossover port. The first lumen may have a distal opening that is more restrictive than a distal opening of the second lumen. Fluid may be inserted into the first lumen, where it flows distally toward the crossover port. When the fluid reaches the crossover port, at least some of the fluid may enter the second lumen where the fluid passes through the distal opening of the second lumen to outside the tubular member. A blocking structure may be disposed near the distal opening of the first lumen, which may at least partially seal the distal opening of the first lumen.

7 Claims, 4 Drawing Sheets

(51) Int. Cl.
*A61B 1/12* (2006.01)
*A61M 3/02* (2006.01)

(58) Field of Classification Search
CPC .... A61B 1/00163; A61B 1/00174; A61B 1/06
USPC ........ 600/104–107, 121–125, 127, 129, 153,
600/156–159, 160, 163–182; 604/19, 21,
604/30, 27, 31, 34, 35, 39, 506, 507, 508,
604/523, 534, 264
See application file for complete search history.

(56) References Cited

U.S. PATENT DOCUMENTS

| | | | |
|---|---|---|---|
| 2005/0272975 A1* | 12/2005 | McWeeney | A61B 1/00071 |
| | | | 600/113 |
| 2007/0249907 A1 | 10/2007 | Boulais et al. | |
| 2008/0255424 A1* | 10/2008 | Durgin | A61B 1/0008 |
| | | | 600/156 |
| 2010/0010310 A1* | 1/2010 | Weisenburgh, II | |
| | | | A61B 1/00091 |
| | | | 600/156 |
| 2011/0319716 A1 | 12/2011 | Naito et al. | |
| 2012/0029279 A1 | 2/2012 | Kucklick | |
| 2013/0267777 A1 | 10/2013 | Avitsian et al. | |
| 2013/0331730 A1* | 12/2013 | Fenech | A61B 1/126 |
| | | | 600/560 |

\* cited by examiner

ELONGATE TUBULAR MEMBER HAVING A CROSSOVER PORT

CROSS-REFERENCE TO RELATED APPLICATIONS

This application claims the benefit of U.S. Provisional Application No. 62/031,455, filed on Jul. 31, 2014. The contents of U.S. Provisional Application No. 62/031,455 are incorporated by reference in their entirety.

TECHNICAL FIELD

The present invention relates generally to systems that delivery fluid to an operation location, and more particularly to an elongate tubular member with a crossover port that communicates fluid between two lumens of the tubular member.

BACKGROUND

An elongate tubular member may be used as part of a system to perform an operation or procedure at an operation location. Part of the operation or procedure may include delivering fluid to the operation location. For example, in medical applications, the tubular member may be an endoscope or catheter, and the operation location may be a treatment site within a patient. Fluid may be delivered to the treatment site as a flushing procedure for various reasons, such as to dilute or thin out viscous fluid or other material, clear an area for visualization, or keep open a stricture or passageway in the body, as examples.

The tubular member may include a plurality of lumens extending in a body of the tubular member, which may be used to perform the operation or procedure. Each of the lumens may be designated, sized, or configured for a particular function associated with the operation or procedure. Minimizing an overall diameter or cross-section of the tubular member while still providing full functionality in order to perform the operation or procedure may be desirable. In that regard, configuring the tubular member to combine functions within the lumens and/or to utilize otherwise unused spaced in the tubular member may be desirable.

BRIEF SUMMARY

In a first aspect, a system may include an elongate tubular member that extends from a proximal portion to a distal portion. The tubular member may include a body that extends from the proximal portion to the distal portion, where the body includes a web. The tubular member may also include a plurality of lumens extending in the body from the proximal portion to the distal portion. The lumens may be separated from each other by the web. The plurality of lumens may include a first lumen having a first distal opening and a second lumen having a second distal opening. The tubular member may further include a crossover port that extends in the web at the distal portion between the first lumen and the second lumen. The first lumen and the second lumen may be in fluid communication with each other via the crossover port. In addition, the tubular member may include an inlet port through which the fluid is inserted into the first lumen. A fluid flow path may extend from the inlet port to the second distal opening of the second lumen via the crossover port.

In a second aspect, a method of delivering fluid through an elongate tubular member may include: inserting fluid into a first lumen of the elongate tubular member; delivering the fluid in the First lumen to a crossover port disposed at a distal portion of the elongate tubular member; passing the fluid through the crossover port into a second lumen of the elongate tubular member; and delivering the fluid in the second lumen from the crossover port to a distal opening of the second lumen, where the fluid exits the elongate tubular member.

In a third aspect, a system may include an elongate tubular member extending from a proximal portion to a distal portion, where the tubular member includes: a body extending from the proximal portion to the distal portion; a plurality of lumens extending in the body from the proximal portion to the distal portion, where the plurality of lumens includes a first lumen having a first distal opening and a second lumen having a second distal opening; a crossover port extending in the body between the first lumen and the second lumen, wherein the first lumen and the second are in fluid communication with each other via the crossover port; and an inlet port through which the fluid is inserted into the first lumen. The system may further include a blocking structure disposed in the first lumen distal the crossover port, wherein the blocking structure at least partially seals the first distal opening of the first lumen.

DETAILED DESCRIPTION

Figure 1:
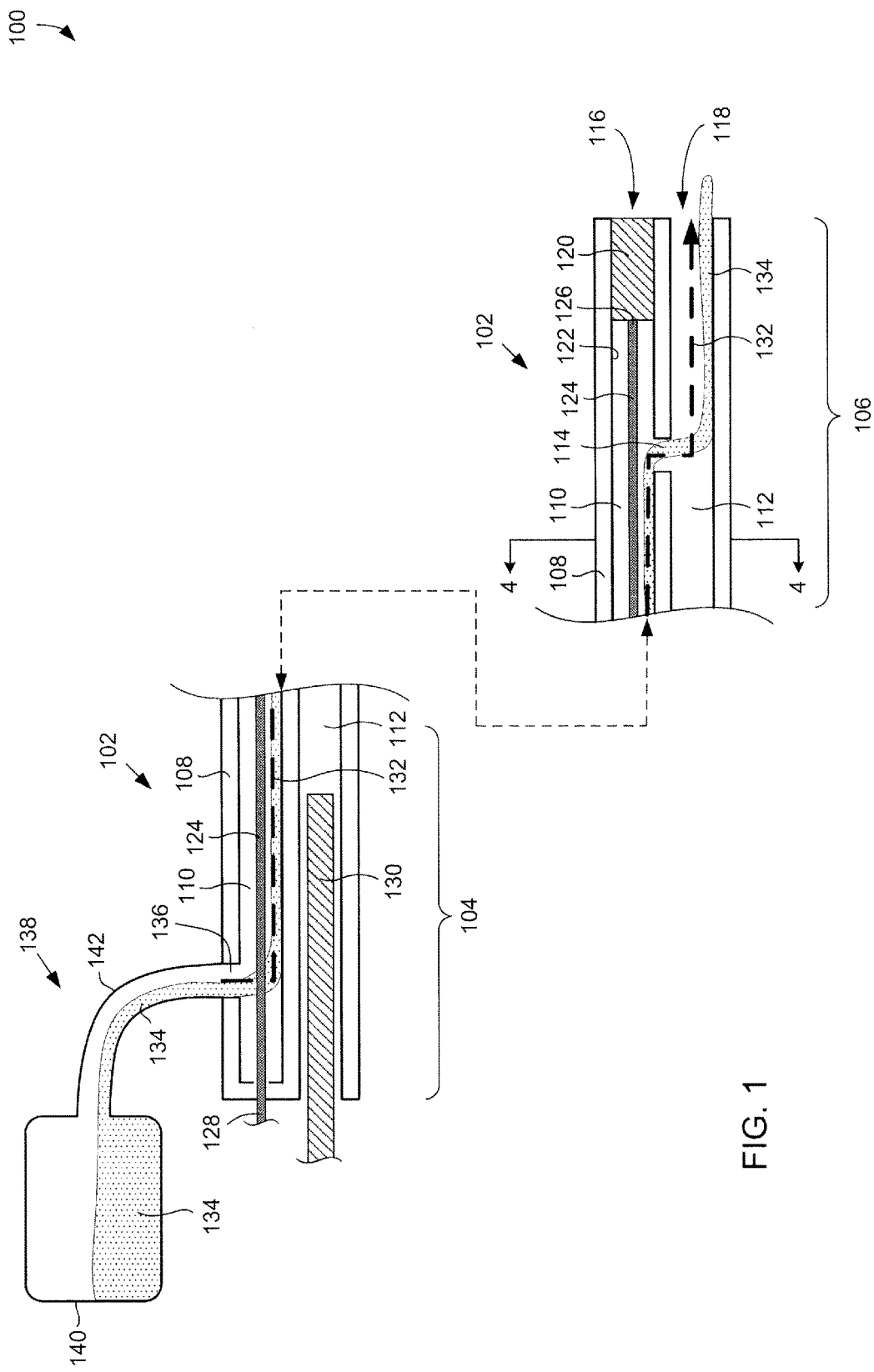
FIG. 1 is a cross-sectional side view of an example system that includes an elongate tubular member, showing fluid being delivered through a distal opening of the tubular member.

The present disclosure describes example systems and devices that include an elongate tubular member with a crossover port that configures two lumens longitudinally extending in a body of the tubular member in fluid communication with each other. A fluid flow path may be established within the tubular member that extends from where fluid is inserted in the first lumen to the distal opening of the second lumen via the crossover port. Fluid may be inserted into the first lumen with the more restrictive distal opening and distally flow toward a distal portion of the tubular member, where at least some of the fluid may flow through the crossover port into the second lumen and exit from the distal opening of the second lumen. The crossover port may be longitudinally disposed in the tubular member at a distal portion such that most or a majority of the fluid flow path extends in the first lumen.

For some example systems, the first lumen may have a more restrictive distal opening than the distal opening of the second lumen. The distal opening of the first lumen may be more restrictive in that it may have a smaller cross-sectional area that is available for fluid to flow through than an available cross-sectional area of the distal opening of the second lumen. For other example systems, the distal opening of the first lumen may be just as restrictive or even less restrictive for fluid to flow through than the distal opening of the second lumen.

For example systems where the distal opening of the first lumen is more restrictive than the distal opening of the second lumen, the first lumen may be otherwise more suitable for fluid delivery than the second lumen with the less restrictive distal opening. For example, the first lumen may have a larger available cross-sectional area for fluid to flow, such as by having an overall larger cross-sectional area, less area occupied by objects other than the fluid, or a combination thereof, which may allow for a greater amount of fluid and/or a greater fluid flow rate of the fluid to flow through the first lumen.

In addition or alternatively, the first lumen with the more restrictive distal opening may be more suitable for fluid delivery because, other than at the distal opening, fewer forces may be acting within that lumen to obstruct fluid flow during an operation or procedure using the tubular member. For example, during an operation or procedure, the second lumen with the less restrictive distal opening may have objects and/or system components moving through the second lumen and/or the number of objects and/or system components moving through the second lumen may change, which may obstruct fluid flow and render difficult fluid delivery through the lumen during the operation or procedure. In contrast, the first lumen with the more restrictive distal opening may not have objects and/or system components disposed in it, or the objects and/or system components in it may not be moving or may be static during an operation or procedure. Accordingly, the first lumen with the more restrictive distal opening may be more suitable for fluid delivery during an operation or procedure involving the tubular member.

Each of the first and second lumens may be configured or designated to perform a function other than fluid delivery. By utilizing the two lumens for fluid delivery in addition to their respective other functions, a lumen specifically designated only for fluid delivery may not be included in the tubular member, which may reduce an overall cross-section of the elongate tubular member.

Example systems having the tubular member with the crossover port may include medical systems, such as endoscopic medical systems, where the elongate tubular member is an endoscope, a catheter, or other similar elongate tubular member configured for insertion into a body of a patient to perform one or more medical procedures at a treatment site within the patient. The first and second lumens may be used to perform the medical procedures. As examples, the first and second lumens may be used to deliver medical devices, fluids, and/or pharmaceuticals to the treatment site; perform aspiration; hold one or more image capture devices and/or one or more light sources, such as at a distal end of the tubular member; and/or communicate power and image data to and from the one or more image capture devices and/or light sources. Other uses of the lumens related to the one or more medical procedures may be possible.

FIG. 1 shows a cross-sectional side view of a system 100 that includes an elongate tubular member 102 longitudinally extending from a first portion 104 to a second portion 106. The tubular member 102 may include a body 108 and a plurality of lumens, including a first lumen 110 and a second lumen 112, longitudinally extending in the body 108. The tubular member 102 may further include a crossover port 114 disposed and extending, such as transversely extending, in between the first lumen 110 and the second lumen 112 at the distal portion 106. The first lumen 110 and the second lumen 112 may be in fluid communication with each other via the crossover port 114.

The first lumen 110 and the second lumen 112 may have respective first and second distal openings 116, 118. The first distal opening 116 of the first lumen 110 may be a more restrictive opening for fluid to flow through than the second distal opening 118. The first distal opening 116 may be more restrictive in that it may have a smaller cross-sectional area that is available for fluid to flow through than an available cross-sectional area of the second distal opening 118.

In the example configuration shown in FIG. 1, the first distal opening 116 may be more restrictive than the second distal opening 118 in that a blocking structure 120 may be disposed within the first lumen 110 at the distal portion 106 of the tubular member 102. The blocking structure 120 may at least partially block fluid from passing through the first distal opening 116. The blocking structure 120 may at least partially block fluid from passing through the first distal opening 116 in that by being disposed in the first lumen 110, a cross-sectional area in between the blocking structure 120 and an inner wall or surface 122 defining the first lumen 110 that is available for fluid to traverse or flow past the blocking structure 120 is less than a total cross-sectional area of the first lumen as defined by the inner surface 122. As described in further detail below, the blocking structure 120 may completely block fluid from passing through the first distal opening 116 such that there is no cross-sectional area in between the blocking structure 120 and the inner surface 122 that is available for fluid to flow through.

At the distal portion 106, the blocking structure 120 may be fixedly disposed in the first lumen 110 and/or attached to the inner wall or surface 122 of the body 108 defining the first lumen 110. The blocking structure 120 may be fixedly disposed and/or attached to the inner wall 122 during delivery of the distal portion 106 to an operation location where the operation or procedure is performed, such as a treatment site within a patient for if the operation or procedure is medical, and/or while the operation or procedure is being performed.

For some example configurations of the system 100, the blocking structure 120 may be an electronic system component or device of the system 100 that is configured to perform a function associated with an operation or procedure involving the tubular member 102. The blocking structure 120, as an electronic system component, may be fixedly disposed or attached in the first lumen 110. Additionally, the blocking structure 120, as an electronic system component, may be contrasted from other system components or devices of the system 100, such as system component or device 130, that may be movably disposed within the second lumen 112 and/or that may not be delivered to the operation location where the operation or procedure is performed until after the distal portion 106 of the tubular member 102 is positioned at the operation location.

An example electronic system component for the block structure 120 may be a visualization system that captures images or video of an area of a surrounding environment surrounding the distal portion 106 during the operation or procedure. Some example configurations of the visualization system may include a combination of an image sensor (such as a complementary metal-oxide-semiconductor (CMOS) image sensor, a charge-coupled device (CCD) sensor, or a fiber-optic based image sensor, as non-limiting examples), a lens, and a visualization system holder configured to hold one or both of the image sensor and the lens. Components other than or in addition to the image sensor, lens, and holder may be included for the visualization system. Another example electronic system component may be a light source (such as a light-emitting diode (LED) or a distal portion of one or more fiber-optic cables as non-limiting examples) that is configured to illuminate an area of the surrounding environment. The light source may be included to enhance visualization and/or image capture performed by the visualization system. A third example electronic system component may be a laser that is configured to output a laser beam or other similar emission of electromagnetic radiation. For example, where the operation or procedure is a medical one, the distal portion 106 of the tubular member 102 may be positioned at a treatment site within a patient, where the laser may be used for treatment. Other electronic system components for the blocking structure 120 that are fixedly disposed in the first lumen 110 and/or attached to the inner wall 122 at the distal portion 106 may be possible.

For some example configurations of the system 100, the blocking structure 120 may be coupled to an elongate inner member 124 longitudinally disposed in the first lumen 110. As shown in FIG. 1, the elongate inner member 124 may longitudinally extend in the first lumen 110 from the proximal portion 104 to the distal portion 106, where a distal end 126 of the elongate inner member 124 may be coupled to the blocking structure 120.

When the blocking structure 120 is an electronic system component or device, the elongate inner member 124 may be an electrically conductive cable electrically coupled to the electronic system component in order for the electronic system component to operate. For example, the conductive cable may be configured to supply power to the electronic system component, communicate image data captured by the electronic system component, communicate command signals to and from the electronic system component, and/or communicate clocking signals to and from the electronic system component. Alternatively, where the electronic system component is a distal portion of one or more fiber-optic cables, the elongate inner member 124 may be a remaining portion of the one or more fiber-optic cables that delivers a light signal to the distal portion.

In alternative configurations, the conductive cabling or wiring may not be needed for the electronic system component to operate, and so elongate inner member 124, as conductive cabling, may not be included. For example, the electronic system component may be a wireless device configured to wirelessly communicate, such as by wirelessly receiving command signals, clocking signals and/or wirelessly transmitting captured image data. In addition or alternatively, the electronic system component may have an internal clock generator and/or an internal power supply (e.g., a battery), in which case the system component may not need to receive power or clocking signals externally from the conductive cabling to operate.

For other example configurations of the system 100, the blocking structure 120 and the elongate inner member 124 may have configurations other than an electronic system component and conductive cable, respectively. For example, the elongate inner member 124 may be configured as a drive wire that is operable to bend or deflect the distal portion 106 of the tubular member 102. The elongate inner member 124, as a drive wire, may be used to navigate or steer the distal portion 106 to an operation location where the operation or procedure is to be performed. Where the elongate inner member 124 is a drive wire, the blocking structure 120 may be configured as an anchoring mechanism that is configured to anchor or secure the distal end 126 of the drive wire 124 to the distal portion 106 of the body 108 of the tubular member 102. The blocking structure 120, as an anchoring mechanism, may be made of an epoxy, solder, or other suitable material to be fixedly attached to the distal end 128 of the drive wire. In addition to anchoring the drive wire 124, the anchoring mechanism 120 may also function as a plug that at least partially plugs the first distal opening 116, which may prevent fluid from passing through the first distal opening 116.

In a third example configuration of the system 100, the blocking structure 120 may be an integral component or part of the body 108 of the tubular member 102. For example, during manufacture of the tubular member 102, the first lumen 110 may be only partially extruded so that the first lumen 110 does not extend all the way to the distal end 122 of the tubular member 102.

Although not shown, a proximal end 128 of the elongate inner member 124 may be operatively coupled to a controller that controls operation of the elongate inner member 124. Where the elongate inner member 124 is a conductive or fiber-optic cable, the controller may be an electronic device that is configured to supply power and/or communicate with the electronic system component via the elongate inner member 124, such as by sending control signals, light signals, and/or clocking signals to the electronic system component, receiving and/or storing captured image data, and/or supplying power to the electronic system component via the conductive or fiber-optic cable. Alternatively, where the elongate inner member 124 is a drive wire, the controller may be a component of a handle used to operate the drive wires.

A fluid flow path identified by dotted line 132 may extend within the tubular member 102 from where fluid 134 is inserted into the first lumen 110, through the crossover port 114 into the second lumen 112, and to the distal opening 118 of the second lumen 112, where the fluid 134 may exit the tubular member 102. As shown in FIG. 1, an inlet port 136 may be configured to receive the fluid 134 from outside the body 108 of the tubular member 102 and communicate the fluid 134 to the first lumen 110. For some example configurations, the inlet port 136 may be disposed in the proximal portion 104 of the tubular member 102 as shown in FIG. 1, although for other example configuration, the inlet port 136 may be disposed in or closer to the distal portion 106. The inlet port 136 may be configured to receive the fluid 134 from a fluid delivery system 138, which may include a fluid source 140 and a channel 142 in fluid communication with the fluid source 140 and the inlet port 136. The fluid source 140 may be configured to hold or contain the fluid 134, and the channel 142 (e.g., a tube, hose, pipe, or other structure operable to deliver fluid) may be configured to deliver the fluid 134 from the fluid source 140 to the inlet port 136. The channel 142 and the 136 may be configured in various ways to deliver the fluid 134 into the first lumen 110. In one example, as shown in FIG. 1, the channel 142 may be connected to the inlet port 136, and the fluid 134 may be delivered through the channel 142 and then through the inlet port 136 before being inserted into the first lumen 110. In alternative examples, an end of the channel 142 may be disposed in the inlet port 136, or alternatively through the inlet port 136 into the first lumen 110. Various configurations of the inlet port 136 and the fluid delivery system 138, including the fluid source 140 and the channel 142, may be possible.

The fluid 134 may be delivered from the fluid source 140 to distally past the distal opening 118 as part of an overall operation or procedure involving the tubular member 102.

For example, delivery of the fluid 134 may be performed as a flushing procedure that is part of the overall operation or procedure. Where the operation or procedure is medical, the fluid 134 may be delivered to a treatment site within a patient where the distal portion 106 is positioned. The fluid may be delivered for various reasons depending on the medical operation or procedure being performed, such as to thin out or lessen the viscosity of a bodily fluid (e.g., bile), open or maintain the opening of an orifice or vessel, or to help clear a pathway (e.g., stones broken into smaller particles from a laser) in order to enhance visualization or illumination, as non-limiting examples.

After the fluid 134 is delivered and/or an operation involving the fluid 134 (e.g., flushing) is performed, an aspiration or suction procedure may be performed to withdraw the fluid 134 (or some combination of the fluid 134 mixed with other fluids, objects, or materials disposed in the operation location) to within the tubular member 102. The fluid 134 may be withdrawn to the proximal portion 104, where the fluid 134 may exit the tubular member 102 and be discarded or otherwise placed in a predetermined location.

Figure 2:
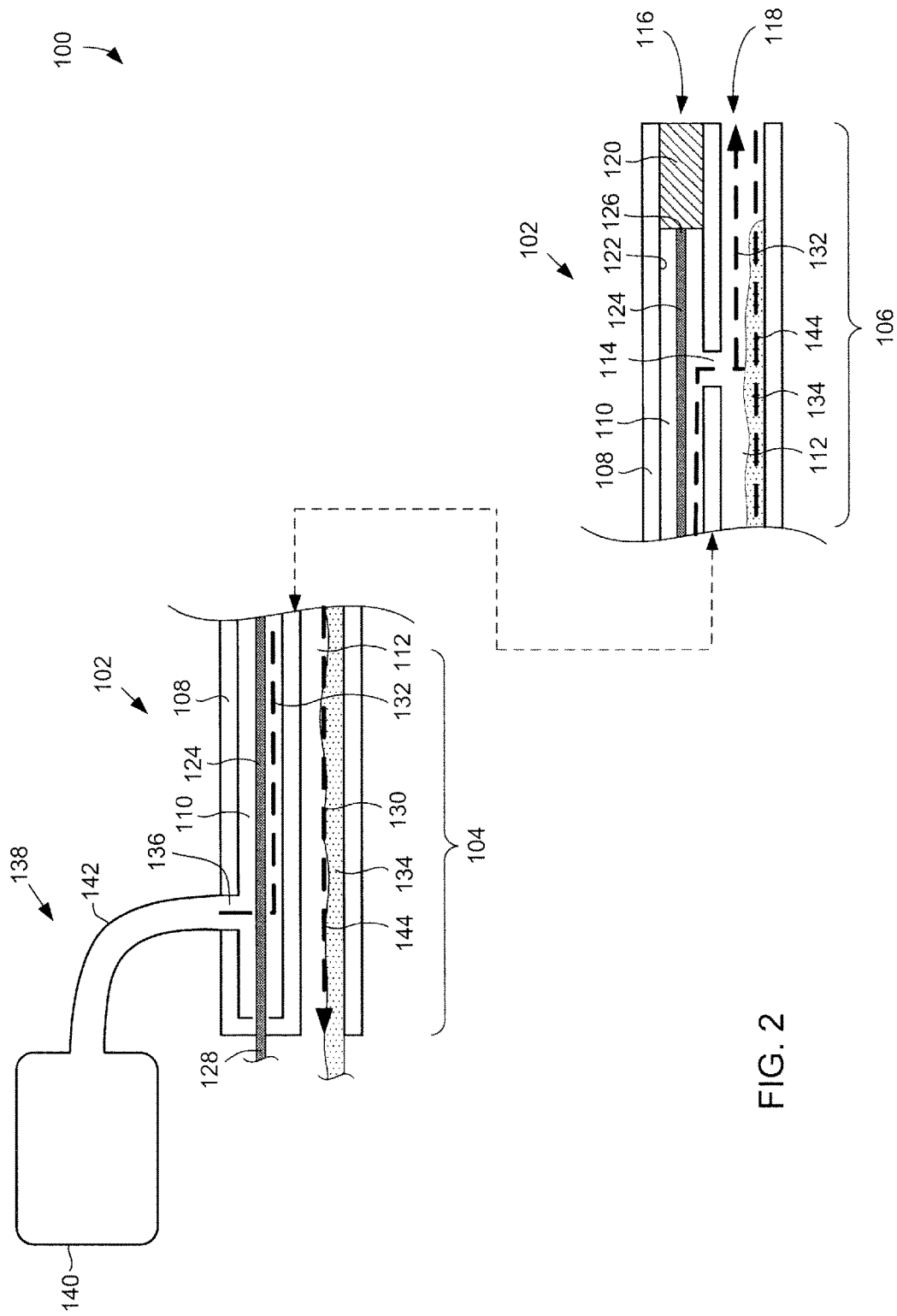
FIG. 2 is a cross-sectional side view of the example system shown in FIG. 1, showing fluid being suctioned back into the tubular member.

For some example configurations, the aspiration or suction procedure may be performed using the second lumen 112, which is shown in FIG. 2. Accordingly, the system 100 may utilize a fluid flow path 132 that is different than an aspiration path as denoted by dotted arrow 144, which extends only in the second lumen 112.

For the example configuration of the system 100 shown in FIG. 1, the blocking structure 120 may seal the first distal opening 116 such that no or substantially no portion of the first distal opening 116 may be available for fluid to flow through. Effectively, then, the first lumen 110 may not have a distal opening for fluid to pass through. As such, if some of the fluid 134 in the first lumen 110 flows past the crossover port 114 toward the blocking structure 120, none of that fluid may pass through the distal opening 116 to outside the tubular member 102.

Figure 3:
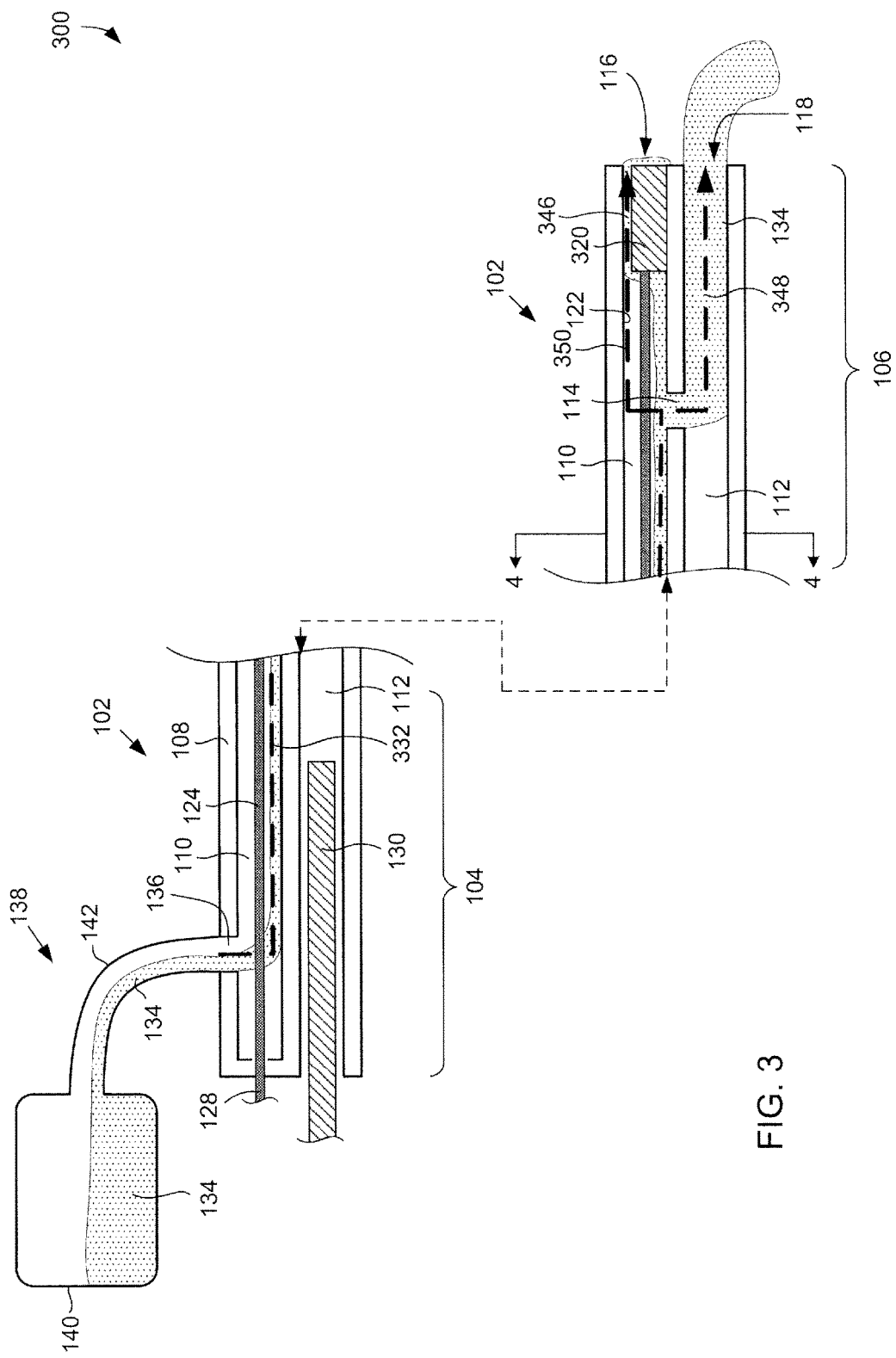
FIG. 3 is a cross-sectional side view of another example system that includes an elongate tubular member, showing fluid being delivered through two distal openings of the tubular member.

FIG. 3 shows another example system 300 that is similar to the example system 100, except that having a blocking structure that completely seals the distal opening 116, the system 300 may have a partial blocking structure 320 disposed in the distal portion 106 that partially seals the distal opening 116 of the first lumen 110. In order to partially seal the distal opening 116, the partial blocking structure 320 may be sized relative to the first lumen 110 such that there is a predetermined amount of space 346 between the partial blocking structure 320 and the inner surface 122 defining the first lumen 110 that is available for a portion of the fluid 134 to pass through to outside the tubular member 102.

Due to the partial seal, a fluid flow path 332 may split into two separate paths at or near the crossover port 114—a first path denoted by dotted arrow 348 that extends through the crossover port 114 into the second lumen 112 to the distal opening 118 as with the fluid flow path 132 of the system 100, and a second path denoted by dotted arrow 350 that extends through the space 346 to the distal opening 116. For some example configurations, a cross-sectional area of the space 346 may be sized smaller than a cross-sectional area of the crossover port 114 and/or a cross-sectional area of the distal opening 118 so that a larger amount of the fluid 134 passes through the crossover port 114 and out of the second lumen 116. For other example configurations, the cross-sectional area of the space 346 may be about the same size or larger than one or both of the cross-sectional areas of the crossover port 114 and the distal opening 118.

The partial blocking structure 320 may be configured to partially seal the distal opening 116 of the first lumen 110 so the portion of the fluid 134 that passes through the space 346 past the distal opening 116 performs a function associated with the partial blocking structure 320. As an example, where the partial blocking structure 320 is a visualization system as previously described, a distal end of the partial blocking structure 320 may include a lens. As shown in FIG. 3, the fluid flowing through the space 346 opening may flow over the distal end of the partial blocking structure 320, which in the case of a visualization system, may clean the lens. Other functions associated with the blocking structure for partially sealing the distal opening 116 may be possible.

For some example configurations, even though the partial blocking structure 320 may only partially seal the distal opening 116, the distal opening 116 of the first lumen 110 may still be more restrictive than the distal opening 118 of the second lumen 112 because the space 346 may provide a smaller available cross-sectional area for fluid to flow through than the available cross-sectional area provided by the distal opening 118. For alternative example configurations, the distal opening 116 may be just as restrictive or even less restrictive than the distal opening 118 for allowing fluid to flow through in that the available cross-sectional area provided by the space 346 may be about the same or greater than the available cross-sectional area provided by the distal opening 118.

Figure 4:
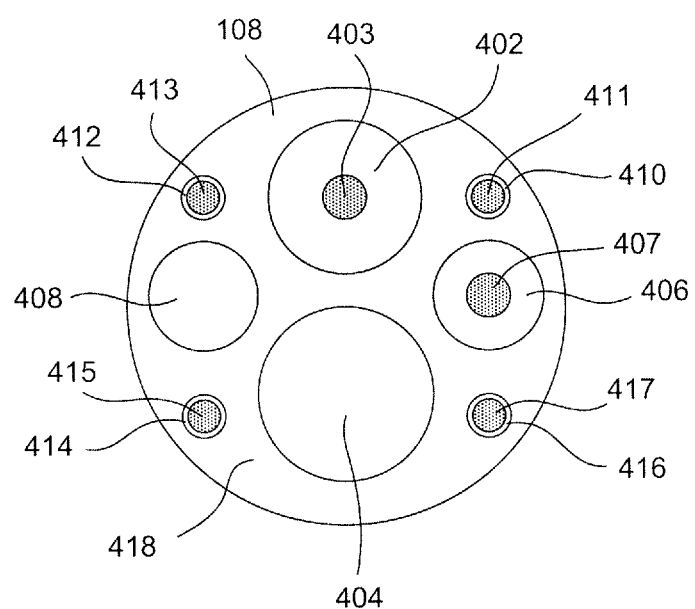
FIG. 4 is a cross-sectional axial view of an example cross-section of the elongate tubular members of the example systems shown in FIGS. 1-3.

FIG. 4 shows a cross-sectional view of an example cross-section of the tubular member 102 taken along lines 4-4 shown in FIGS. 1 and 3. As shown in FIG. 4, the tubular member 102 may include eight lumens. Each of the eight lumens may be dedicated for a particular function associated with an operation or procedure involving the tubular member 102. A first lumen 402 may be a visualization lumen that is configured to have a visualization system disposed within it. For some example configurations, a conductive cable 403 may be disposed within the visualization lumen 402 that includes one or more wires to supply power and/or communicate signals (data signals, command signals, clocking signals, etc.) between a visualization system and one or more external electronic devices. A second lumen 404 may be a first or primary working channel or lumen that is configured to deliver system components or devices to and from an operation location where the operation or procedure involving the tubular member 102 is performed. For medical applications, the system components or devices may be medical devices used to perform the medical procedure.

A third lumen 406 may be a light lumen that designated for a light source that provides illumination at the operation location. The light lumen 406 may include an elongate inner member 407 having a configuration that may depend on the type of light source being used. For example, the elongate inner member 407 may be a fiber-optic cable or a wire to supply power to a LED as non-limiting examples.

A fourth lumen 408 may be a second (or secondary) working channel or lumen that, like the first working channel 404, may be configured to deliver system components or deices to and from an operation location where the operation or procedure involving the tubular member 102 is performed. Alternatively, the fourth lumen 408 may be a second light lumen. Fifth through eighth lumens 410, 412, 414, and 416 may each be drive wire lumens configured to have disposed within a respective drive wire 411, 413, 415, 417 that is operable to bend or deflect the distal portion 106 of the tubular member 102, as previously described. Alternative example cross-sections of the tubular member 102 may include numbers of lumens other than eight. At the very least, the tubular member 102 includes two lumens.

As shown in FIG. 4, the body 108 of the tubular member 102 may include a web 418 that separates or isolates the lumens 402-416 from each other. The crossover port 114 (FIGS. 1-3) may extend in a portion of the web 418 such that two of the lumens 402-416 are in fluid communication with each other via the crossover port 114.

The two lumens that are in fluid communication with each other via the crossover port may correspond to the first and second lumens 110, 112 shown in FIGS. 1-3. One of the lumens may have a fixedly attached blocking structure disposed within it at the distal portion and/or that has a more restrictive distal opening than the distal opening of the other lumen. Representative lumens for the first lumen 110 having the blocking structure and/or with the more restrictive distal opening 116 may include the visualization lumen 402, the light lumen 406, or any of the drive wire lumens 410-416. Each of these lumens may have disposed within at the distal portion 106 a blocking structure that at least partially restricts fluid flow through a distal opening of the lumen in which it is disposed. Representative lumens for the second lumen 112 that does not a fixedly attached blocking structure and/or that has a less restrictive distal opening 118 may include the first working channel 404, the light lumen 406, and the second working channel or second light lumen 408.

A light lumen may be used for the first lumen 110 or the second lumen 112, depending on the type of light source used and/or which lumen is designated as the other lumen. For example, if the light source does not take up the entire cross-sectional area of the light lumen (e.g., the light source is a fiber optic cable with a diameter smaller than the diameter of the light lumen), then the distal opening of the light lumen may be less restrictive than a lumen having a distal opening that is sealed or substantially sealed, such as the visualization lumen 402 or the drive wire lumens 410-416. Alternatively, if the light source seals or substantially seals the distal opening of the light lumen or otherwise has a more restrictive distal opening than the other lumen (e.g., a working channel), then the light lumen may be the first lumen 110 with the more restrictive distal opening.

The present description also describes an example method of operating an elongate tubular member with a crossover port disposed between two lumens of the tubular member. Description of the method is made with reference to the elongate tubular member 102 shown in FIGS. 1-4. The example method may include distally advancing the tubular member 102 until the distal portion 106 of the tubular member 102 is positioned at an operation location where an operation or procedure involving the tubular member 102 is to be performed. One or more drive wires, such as drive wires 411-417, may be operated to deflect the distal portion 106 in order to navigate or steer the tubular member 102 to the operation location. For medical applications, the operation location may be a treatment site within a patient.

After the distal portion 106 of the tubular member 102 is advanced to and positioned at the operation location, the procedure or operation involving the tubular member 102 may be performed. The operation or procedure may include performing one or more actions on one or more target objects located at the operation location. One or more system components or devices, such as system component 130 shown in FIG. 1, may be delivered to the operation location to perform the one or more actions. The one or more system components may be delivered to the operation location via the second lumen 112, which may be the primary working channel 404 or the secondary working channel 408. Where the operation or procedure is medical, the system component 130 may be a medical device that is used to perform an action on a target tissue or other biological or cellular structure within the patient at the treatment site, such as obtaining a tissue sample, performing an electrosurgical procedure on target tissue, removing stones, inserting a stent, delivering pharmaceuticals, or any other medical procedure involving a tubular member.

The example method may also include capturing images of the surrounding environment and the procedure or operation being performed with a visualization system disposed in a visualization lumen, such as visualization lumen 402. In addition, the example method may include illuminating the surrounding environment using a light source disposed in a light lumen, such as light lumen 406. Illuminating the surrounding environment may enhance visualization of the surrounding environment and/or the operation or procedure being performed.

The example method may further include delivering the fluid 134 to the operation location, either as part of or during the operation or procedure. The fluid 134 may be delivered from a fluid delivery system 138 located external the tubular member 102 through the inlet port 136 and into the first lumen 110. The fluid 134 may distally flow along the fluid flow path 132, 332 in the first lumen 110 to the crossover port 114. For some example methods, the fluid 134, while distally flowing in the first lumen 110, may flow around the elongate inner member 124 that is disposed in the first lumen 110. Example configurations of the elongate inner member 124 may include a conductive or fiber-optic cable or a drive wire, depending on which lumen is designated as the first lumen 110, as previously described. Where the elongate inner member 124 is a conductive or fiber-optic cable, the fluid 134 may flow around the cable while power, light signals, data signals, clocking signals, and/or command signals are being communicated through the cable.

When the fluid reaches the crossover port 114, at least some of the fluid 134 may flow through the crossover port 114 into the second lumen 112. The portion of the fluid 134 that flowed through the crossover port 114 may thereafter exit the distal opening 118 of the second lumen 112 to outside the tubular member 102. For some example methods, at least some of the fluid 134 inserted into the first lumen 110 may remain in the first lumen 110 instead of flowing through the crossover port 114 into the second lumen 110. As previously described, a blocking structure 120 or a partial blocking structure 320 may be disposed in the first lumen 110 that at least partially seals the distal opening 116 of the first lumen 110. The portion of the fluid 134 that remains in the first lumen 110 may flow to the blocking structure 120 or the partial blocking structure 320. Where the blocking structure 120 is disposed in the first lumen 110 and the first lumen 110 is completely sealed, the portion of the fluid 134 that did not enter the crossover port 114 may contact the blocking structure 120 but not flow through the distal opening 116 due to distal opening 116 being completely sealed. The fluid may then either remain in the first lumen 110 or eventually flow into the crossover port 114. Alternatively, where the partial blocking structure 320 is disposed in the first lumen 110 and the distal opening 116 is only partially sealed, at least some of the fluid 134 that did not initially flow into the crossover port 114 may flow through the space 346 in between the partial blocking structure 320 and the inner surface 122 defining the first lumen 110. The portion of the fluid 134 that entered the space 346 may flow past the distal opening 116 of the first lumen 110 to outside the tubular member 102. The portion of the fluid 134 may continue to flow over a distal end of the partial blocking structure 320. As previously described, the portion of the fluid 134 that flows over the distal end of the partial blocking structure 320 may perform a function associated with the partial blocking structure 320. For example, the distal end of the partial blocking structure 320 may include a lens, in which case the fluid may clean the lens.

For some example methods, one or more system components movable in the second lumen 112 may be moved or positioned proximal the crossover port 114 before the fluid 134 is inserted into the first lumen 110, delivered in the first lumen 110 to the crossover port 114, and/or passed through the crossover port 114 into the second lumen 112 so that the distal opening 118 of the second lumen 112 has enough available area for the fluid to flow through it. Alternatively, the distal opening 118 may have enough available area for fluid to flow through it even with the one or more system components positioned in the second lumen 112, and so the one or more system components may not be moved proximal the crossover port 114 and/or may be maintained in their position in the distal opening 118 of the second lumen 112.

After the fluid 134 flows outside of the tubular member 102 at the operation location, either through the distal opening 118 or both of the distal openings 116 and 118, the example method may further include aspirating or suctioning the fluid 134 back through the second opening 118 into the second lumen 112, through which the fluid 134 may be withdrawn back to the proximal portion 104 to outside the tubular member 102, where the fluid 134 may be discarded, disposed of, or otherwise placed in a predetermined location. When the procedure or operation is finished, the method may further include proximally withdrawing the tubular member 102 away from the operation location.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A system comprising: an elongate tubular member extending from a proximal portion to a distal portion, the tubular member comprising: a body extending from the proximal portion to the distal portion, wherein the body comprises a web; a plurality of lumens extending in the body from the proximal portion to the distal portion and separated from each other by the web, the plurality of lumens comprising a first lumen having a first distal opening and a second lumen having a second distal opening, wherein the second distal opening is configured to permit flow of a fluid therethrough; an electronic system component disposed in the first lumen at the distal portion, wherein the electronic system component at least partially seals the first distal opening; wherein the electronic system component comprises one of a visualization system, a light source, or a laser; a crossover port extending in the web at the distal portion between the first lumen and the second lumen, wherein the first lumen and the second lumen are in fluid communication with each other via the crossover port; an inlet port through which the fluid is inserted into the first lumen; and a fluid flow path that extends from the inlet port to the second distal opening of the second lumen via the crossover port.

2. The system of claim 1, wherein the electronic system component completely seals the first distal opening.

3. The system of claim 1, further comprising an elongate inner member longitudinally extending in the first lumen and coupled to the electronic system component.

4. The system of claim 1, further comprising a cable longitudinally extending in the first lumen and coupled to the electronic system component, wherein the cable is configured to communicate one or more of a power supply, a light signal, a data signal, a clocking signal, or a command signal with the electronic system component.

5. The system of claim 1, wherein the electronic system component only partially seals the first distal opening, wherein a space for fluid flow is disposed in between the electronic system component and an inner surface that defines the first lumen, and wherein the fluid flow path separates into a first branch and a second branch at the distal portion, the first branch extending through the crossover port to the second distal opening of the second lumen, and the second branch extending through the space to the first distal opening.

6. The system of claim 1, wherein the first lumen comprises one of: a visualization lumen, wherein the electronic system component comprises the visualization system disposed within at the distal portion; or a light lumen, wherein the electronic system component comprises the light source disposed within at the distal portion.

7. The system of claim 1, wherein the first distal opening is either as restrictive or more restrictive for passage of fluid than the second distal opening.

* * * * *